United States Patent [19]

Sasaki

[11] Patent Number: 4,658,632

[45] Date of Patent: Apr. 21, 1987

[54] SENSOR

[75] Inventor: Kazuko Sasaki, Hiroshima, Japan

[73] Assignees: Figaro Engineering Inc.; Mazda Motor Corporation, both of Japan

[21] Appl. No.: 807,257

[22] Filed: Dec. 10, 1985

[30] Foreign Application Priority Data

Dec. 20, 1984 [JP] Japan .................................. 59-270252

[51] Int. Cl.⁴ ............................................ G01N 27/12
[52] U.S. Cl. ........................................... 73/23; 338/34
[58] Field of Search .................... 73/23, 27 R; 338/34; 324/71.5; 340/634; 422/98

[56] References Cited

U.S. PATENT DOCUMENTS

| | | | |
|---|---|---|---|
| 4,314,996 | 2/1982 | Sekido et al. | 338/34 |
| 4,507,643 | 3/1985 | Sunano et al. | 338/34 |
| 4,601,883 | 7/1986 | Sekido et al. | 338/34 |

Primary Examiner—Stephen A. Kreitman
Attorney, Agent, or Firm—Kane, Dalsimer, Kane, Sullivan and Kurucz

[57] ABSTRACT

A λ sensor comprising a perovskite compound $ASnO_{3-\delta}$ and silica, germania, zirconia or hafnia added to the compound in an amount of 0.5 to 30 mol % per mol of the compound. Silica or like additive gives improved oxygen sensitivity and reduces the temperature dependence of the oxygen sensitivity.

8 Claims, 8 Drawing Figures

SENSOR

BACKGROUND OF THE INVENTION

1. Field of the Invention

The present invention relates to improvements in λ sensors for detecting the air/fuel ratio or equivalent ratio λ of exhaust gases, and more particularly to a λ sensor utilizing variations in the resistance value of a metallic oxide semiconductor. The λ sensor of the present invention is suitable for controlling internal combustion engines such as motor vehicle engines and for controlling combustion devices such as air heaters, boilers and the like.

2. Prior Art

The present inventor has discovered that compounds such as $BaSnO_{3-\delta}$, $RaSnO_{3-\delta}$, $CaSnO_{3-\delta}$ and $SrSnO_{3-\delta}$ exhibit outstanding characteristics as λ sensors (Japanese Patent Applications SHO No. 59-63900 and SHO No. 59-63901, corresponding U.S. patent application Ser. No. 711,154 and corresponding European Patent Application No. 85103,512). These compounds have the crystalline structure of the perovskite type and are novel λ sensor materials. They have the features of being highly durable against high-temperature reducing atmospheres and highly sensitive to variations in oxygen partial pressure. They have another feature in that the sensitivity to combustible gases and the sensitivity to oxygen are relatively in good balance.

To mention related prior-art references, Examined Japanese Patent Publication SHO No. 50-23317 (corresponding to U.S. Pat. No. 3,644,795 and West German Patent No. 2,062,574) discloses that the addition of silica binder to $SnO_2$ affords a gas sensor of improved mechanical strength without impairing air permeability.

U.S. Pat. No. 4,225,559 further discloses that the addition of Pt-Rh catalyst to $TiO_2$ provides a sensor of improved responsiveness to changes of atmosphere.

SUMMARY OF THE INVENTION

An object of the present invention is to provide a λ sensor having an enhanced oxygen sensitivity which is less dependent on the temperature.

Another object of the present invention is to prevent diminution of the air/fuel ratio detection accuracy due to unreacted combustible gases.

The λ sensor of the present invention detects air/fuel ratios λ according to variations in the resistance value of a compound $ASnO_{3-\delta}$ wherein A is at least one of Ra, Ba, Sr and Ca, and δ is a non-stoichiometric parameter. The compound $ASnO_{3-\delta}$ has added thereto the dioxide of at least one element selected from the group consisting of silicon, germanium, zirconium and hafnium, in an amount of 5 to 300 mmols per mol of the compound.

The concept of oxygen gradient will be considered. When the resistance value Rs of the sensor is expressed by $Rs = K \cdot P_{O_2}^m$, m represents the oxygen gradient. The theoretical upper limit of the oxygen gradient for n-type semiconductors, i.e. semiconductors whose resistance value increases with oxygen partial pressure, is $\frac{1}{4}$ or 1/6. With p-type semiconductors, i.e., semiconductors whose resistance value decreases with oxygen partial pressure, the upper limit is $-\frac{1}{4}$ or -1/6. The value of $\frac{1}{4}$ is obtained from a model of n-type semiconductor wherein lattice $O^{2-}$ ion changes to a defect trapping one electron, one free electron and $\frac{1}{2}$ gas-phase oxygen molecule. From a model wherein the ion is in equilibrium with a defect trapping no electron, two free electrons and $\frac{1}{2}$ gas-phase oxygen molecule, the value of 1/6 is obtained. Similar p-type semiconductor modles give the theoretical value of $-\frac{1}{4}$ or -1/6.

In the case of the compound $ASnO_{3-\delta}$, the value of oxygen gradient is about 0.18 if it is best, and the oxygen gradient can be improved by about 0.03 to about 0.04 by the addition of $SiO_2$ or the like. This variation, which may be small, can be evaluated as a very great change considering that the value of oxygen gradient is close to the theoretical upper limit. At any rate, an improvement in the oxygen gradient greatly improves the characteristics of the λ sensor.

In addition to $SiO_2$, $GeO_2$, $ZrO_2$ and $HfO_2$ are effective for improving the oxygen gradient. These dioxides are equivalent to one another. These compounds produce an improved effect when used in a relatively large amount. The dioxide must be added in an amount of at least 5 mmols, preferably at least 20 mmols, per mol of the compound $ASnO_{3-\delta}$. The effect due to the addition of the dioxide levels off when the amount increases to about 50 mmols. The upper limit of the amount of the dioxide has no substantial significance but is determined from the fact that a greatly increased amount, if used, gives high resistance to the sensor and renders the sensor difficult to handle.

The term "silica" as used herein does not mean an oxide containing elemental silicon but means the dioxide of silicon. This is also true of germanium, zirconium and hafnium.

The addition of $SiO_2$, $GeO_2$ or the like is also effective for diminishing the temperature dependence of the oxygen sensitivity. The oxygen sensitivity of $BaSnO_{3-\delta}$ and $RaSnO_{3-\delta}$ decreases with temperature, while the oxygen sensitivity of $CaSnO_{3-\delta}$ and $SrSnO_{3-\delta}$ increases with temperature. Presence of $SiO_2$, $GeO_2$, $HfO_2$ or $ZrO_2$ decreases the temperature dependence of the oxygen sensitivity. This means diminution of the error due to temperature.

The oxygen gradient of the compound $ASnO_{3-\delta}$ improves with the growth of crystals. The mean crystallite size of the compound $ASnO_{3-\delta}$, although not limitative specifically, is preferably 0.02 to 25 μ, more preferably 0.15 to 8 μ. The oxygen gradient is improved by the growth of crystals independently of the improvement thereof by the addition of $SiO_2$ or the like.

Of the compounds $ASnO_{3-\delta}$, $BaSnO_{3-\delta}$ and $RaSnO_{3-\delta}$ are completely n-type semiconductors and are greater than $CaSnO_{3-\delta}$ and $SrSnO_{3-\delta}$ in the absolute value of oxygen gradient. Accordingly, the most preferred compounds are $BaSnO_{3-\delta}$ and $RaSnO_{3-\delta}$ and such compounds wherein Ba or Ra is partially replaced by Ra or Ba, e.g., $Ba_{0.5}Ra_{0.5}SnO_{3-\delta}$.

On the other hand, $CaSnO_{3-\delta}$ and $SrSnO_{3-\delta}$ are peculiar compounds which exhibit n-type properties in response to the change from λ<1 to λ>1 in the vicinity of the point of equivalence but exhibit p-type properties in response to variations in the lean burn region of λ>1 and become negative in oxygen gradient.

In practicing the present invention, care should be taken, although not in a limitative sense, to hold the sensitivity to combustible gases in balance with the sensitivity to oxygen. The compound $ASnO_{3-\delta}$, although relatively low in sensitivity to combustible gases, is more sensitive to combustible gases than to oxygen. Accordingly the λ value detected is lower than the actual value in the presence of an unburnt combustible gas. To avoid this problem, it is preferable to add a noble metal such as Pt to the compound $ASnO_{3-\delta}$ in an amount of 20 μg to 3 mg per gram of the compound. Presence of a large amount, e.g., 10 mg, of such metal results in impaired responsiveness to changes of atmosphere. The addition of noble metal produces an effect which is independent of the effect of $SiO_2$ or the effect of growth of crystals and exerts little or no influence on the sensitivity to oxygen.

DESCRIPTION OF THE PREFERRED EMBODIMENT

Preparation of Materials $BaCO_3$, $RaCO_3$, $SrCO_3$ or $CaCO_3$, and $SnO_2$ in equal mol amounts are mixed together and calcined in air at 900° C. or 1100° C. for 4 hours. The product is a perovskite compound, i.e., $BaSnO_{3-\delta}$, $RaSnO_{3-\delta}$, $CaSnO_{3-\delta}$ or $SrSnO_{3-\delta}$. Incidentally, a magnesium compound or beryllium compound, even if reacted with $SnO_2$, will not be converted to $MgSnO_{3-\delta}$ or $BeSnO_{3-\delta}$.

Figure 8:
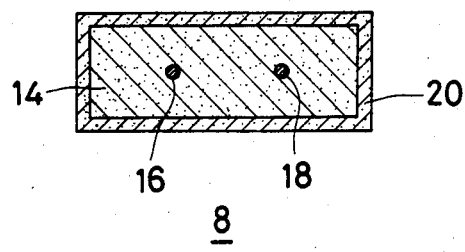
FIG. 8 is an enlarged view in section showing a gas sensor piece.

The calcined product is pulverized, and 1 to 20 mol % of silica colloid, germanium hydroxide, hafnium hydroxide or zirconium hydroxide is added to the product. The term "mol %" means the amount added to the compound $ASnO_{3-\delta}$ in terms of mol % per 100 mol % of the compound. The mixture is moled into a gas sensor piece as shown in FIG. 8 and baked in air for 4 hours at a temperature of 1000° or 1100° C. when the starting mixture is calcined at 900° C., or at a temperature of 1200° to 1800° C. if the starting mixture is calcined at 1100° C.

The baking atmosphere is not limited to air but may be a neutral atmosphere, for example, of $N_2$ or an oxidizing atmosphere, for example, of 100% $O_2$, provided that it is not a reducing atmosphere. While desired materials are usable as silica and like starting materials, preferred materials are in the form of sol, gel or like colloid or hydroxide.

The silica colloid, germanium hydroxide or the like added is converted to silica, germania or the like. Such oxide is distributed in the form of fine particles of large surface area throughout the sensor.

For comparison, silica colloid is replaced by stannic acid colloid or titanium hydroxide to prepare specimens. Further 5 wt. % borosilicate glass (80 wt. % $SiO_2$, 13 wt. % $B_2O_3$, 4 wt. % $N_2O$, and balance $Al_2O_3$ and $K_2O$) is similarly used to obtain a specimen.

When specimens incorporating a noble metal such as Pt, Rh, Ir, Os, Ru or Pd are to be prepared, the specimen resulting from baking is impregnated with a compound of noble metal salt and baked at 950° C. for 2 hours to cause the compound $ASnO_{3-\delta}$, and $SiO_2$ or the like to support the noble metal. The noble metal compound is used in an amount of 30 μg to 10 mg, calculated as the noble metal, per gram of the compound $ASnO_{3-\delta}$. In the following description, the amount of 1 μg per gram of the compound $ASnO_{3-\delta}$ will be expressed as 1 ppm.

$ASnO_{3-\delta}$ vs. $SnO_2$ $SnO_2$ is used as a known λ sensor material for comparison with the compound $ASnO_{3-\delta}$. The $SnO_2$ is prepared by calcination at 1100° C., followed by baking at 1400° C.

Comparison between $BaSnO_{3-\delta}$ and $SnO_2$ reveals that the former is remarkably improved in endurance to a reducing atmosphere at a high temperature, with the combustible gas sensitivity nearly in balance with the $O_2$ balance. $RaSnO_{3-\delta}$, $SrSnO_{3-\delta}$ and $CaSnO_{3-\delta}$ are similarly effective in giving improved endurance and inhibiting the combustible gas sensitivity.

TABLE 1

$BaSnO_{3-\delta}$ vs. $SnO_2$

| Specimen | Reduction of resistance due to endurance test (Rso/Rsf)*[1] | CO sensitivity*[2] ($R_s$co1000/$R_s$co10,000) | Oxygen gradient*[3] (at 700° C.) |
| --- | --- | --- | --- |
| $BaSnO_{3-\delta}$ + $SiO_2$ 5 mol % 1400° C. baking | 1.0 | 1.9 | 0.22 |
| $BaSnO_{3-\delta}$ + $SiO_2$ 5 mol % 1400° C. baking + Pt 100 ppm*[4] | 1.0 | 1.02 | 0.22 |
| $SnO_2$ + $SiO_2$ 5 mol % 1400° C. baking | Up to 10 | Up to 3 | 0.20 |
| $SnO_2$ + $SiO_2$ 5 mol % 1400° C. baking + Pt 100 ppm | Up to 10 | Up to 3 | 0.20 |

*[1] At 900° C. for 4 hours, the specimen is subjected to repeated cycles of 4-second period including 3 seconds in an atmosphere of λ = 0.8 and 1 second in an atmosphere of λ = 0.9. The specimen is then exposed to an atmosphere of λ = 1.05 at 700° C. and checked for the resulting variation in resistance value to determine the ratio of the initial resistance value to the value after the endurance test.
*[2] The ratio of the resistance value at 1,000 ppm of CO to that at 10,000 ppm of CO, as determined at 700° C. in a system containing 4.6% of oxygen and $N_2$ in balance.
*[3] The variation in the resistance value due to the change in $O_2$ concentration from 1% to 10%, as evaluated using $Rs = K \cdot PO_2{}^m$.
*[4] The amount added of 1 μg per gram of the semiconductor is expressed as 1 ppm (the same as hereinafter).

Figure 1:
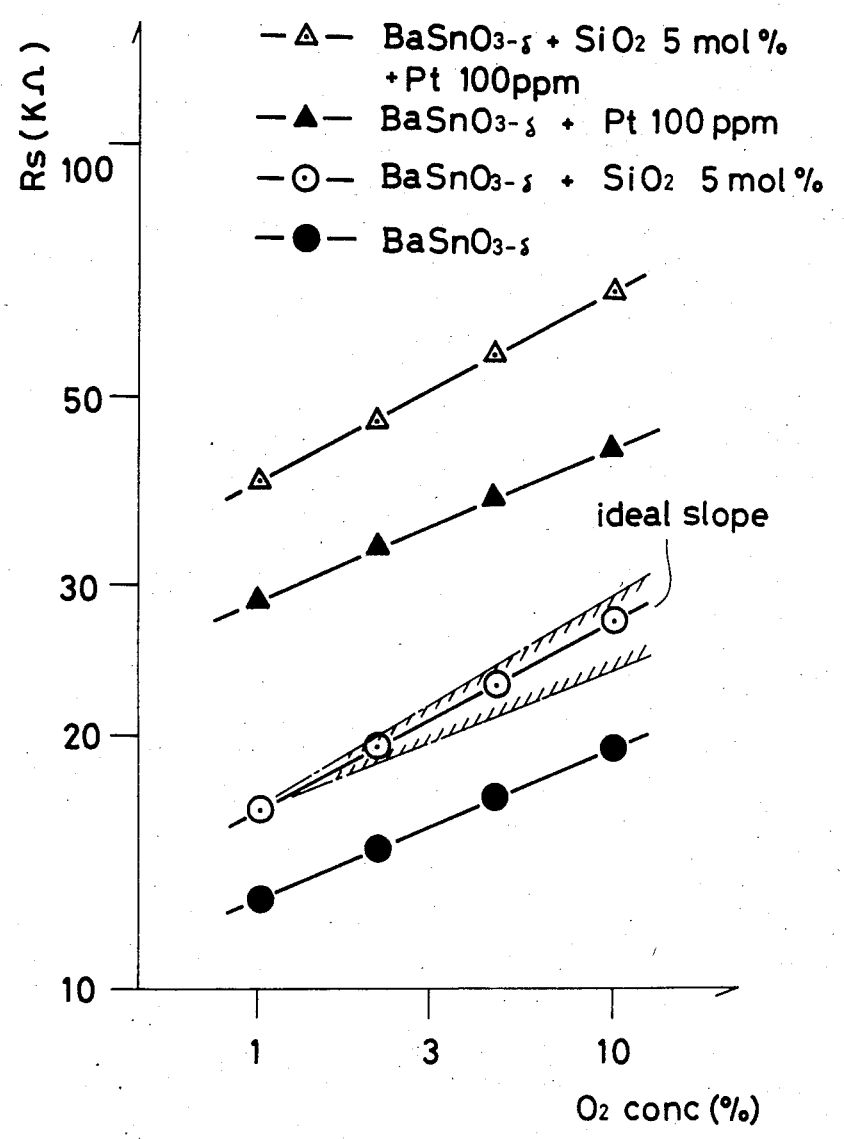
FIG. 1 is a characteristics diagram showing the relation between the resistance value of $BaSnO_{3-\delta}$ and oxygen concentration at 700° C.

Effect of SiO₂ or the Like $BaSnO_{3-\delta}$ baked at 1400° C. is checked for variations in the oxygen gradient at 700° C. due to the addition of $SiO_2$. FIG. 1 shows the result. The addition of 5 mol % of $SiO_2$ improves the oxygen gradient from 0.18 to 0.22. Pt, if added, produces no effect on the oxygen gradient. Table 2 shows the results achieved by using varying amounts of $SiO_2$ and also by using $GeO_2$, $ZrO_2$ or $HfO_2$ in place of $SiO_2$. Use of a mixture of $SiO_2$ and $GeO_2$, or the like produces a similar result.

TABLE 2

Effect of addition of $SiO_2$ or the like

| No.*1 | Semiconductor*2 | Amount added (mol %) | Oxygen gradient*3 600° C. | 700° C. | 800° C. | Resistance at λ = 1.01 (700° C., kΩ) |
|---|---|---|---|---|---|---|
| 1* | $BaSnO_{3-\delta}$ |  | 0 | 0.203 | 0.182 | 0.176 | 12 |
| 2 | $BaSnO_{3-\delta}$ | $SiO_2$ | 1 | 0.212 | 0.210 | 0.207 | 13 |
| 3 | $BaSnO_{3-\delta}$ | $SiO_2$ | 3 |  | 0.217 |  |  |
| 4 | $BaSnO_{3-\delta}$ | $SiO_2$ | 5 | 0.217 | 0.220 | 0.218 | 15 |
| 5 | $BaSnO_{3-\delta}$ | $SiO_2$ | 10 | 0.220 | 0.221 | 0.221 | 30 |
| 6 | $BaSnO_{3-\delta}$ | $SiO_2$ | 20 |  | 0.219 |  | 70 |
| 7* | $RaSnO_{3-\delta}$ |  | 0 | 0.214 | 0.193 | 0.181 |  |
| 8 | $RaSnO_{3-\delta}$ | $SiO_2$ | 5 | 0.223 | 0.224 | 0.223 |  |
| 9* | $SrSnO_{3-\delta}$ |  | 0 | −0.09 | −0.12 | −0.15 |  |
| 10 | $SrSnO_{3-\delta}$ | $SiO_2$ | 5 | −0.16 | −0.17 | −0.17 |  |
| 11* | $CaSnO_{3-\delta}$ |  | 0 | −0.11 | −0.15 | −0.16 |  |
| 12 | $CaSnO_{3-\delta}$ | $SiO_2$ | 5 | −0.18 | −0.18 | −0.18 |  |
| 13 | $BaSnO_{3-\delta}$ | $GeO_2$ | 5 | 0.216 | 0.215 | 0.213 |  |
| 14 | $BaSnO_{3-\delta}$ | $ZrO_2$ | 5 | 0.217 | 0.216 | 0.218 |  |
| 15 | $BaSnO_{3-\delta}$ | $HfO_2$ | 5 | 0.219 | 0.214 | 0.217 |  |
| 16 | $BaSnO_{3-\delta}$ | $SiO_2$ + Pt | 5 / 100 ppm | 0.217 | 0.221 | 0.217 |  |
| 17 | $BaSnO_{3-\delta}$ | $SiO_2$ + Pt | 5 / 1000 ppm | 0.216 | 0.214 | 0.219 |  |
| 18* | $BaSnO_{3-\delta}$ | $SnO_2$ | 5 |  | 0.179 |  |  |
| 19* | $BaSnO_{3-\delta}$ | $TiO_2$ | 5 |  | 0.181 |  |  |
| 20* | $BaSnO_{3-\delta}$ | Borosilicate glass (5 wt. %) |  |  | 0.12 |  |  |

*1 The * mark indicates comparative example.
*2 The semiconductor is baked at 1400° C., and no noble metal is added.
*3 The value of m as determined from $Rs = K.O_2^m$ based on the variation in the resistance value due to the change in $O_2$ concentration from 1% to 10%.

The addition of $SiO_2$ to any of the sensor compounds increases the absolute value of the oxygen gradient. Even if 1 mol % of the dioxide is present, a considerably great effect is available, while the effect levels off when the amount increases beyond 5 mol %. The experiments conducted show that addition of up to 30 mol % is desirable since an increase in the amount added results in the drawback of giving higher resistance to the sensor.

$GeO_2$, $ZrO_2$ and $HfO_2$ are equivalent in effectiveness to $SiO_2$, whereas $SnO_2$ or $TiO_2$ are ineffective. The addition of borosilicate glass conversely reduces the oxygen sensitivity.

The second effect achieved by the addition of $SiO_2$ or the like is a reduction in the temperature dependence of the oxygen gradient. This means diminution of one of error factors due to temperature variations.

Effect of Growth of Crystals

Table 3 shows the effect of the growth of crystals on the oxygen gradient with reference to some of the compounds $ASnO_{3-\delta}$ having added thereto 5 mol % of $SiO_2$. With any of these compounds, the absolute value of the oxygen gradient increases with the growth of crystals. A critical improvement is achieved when the mean crystallite size is not smaller than 0.15 μ.

The mean crystallite size herein referred to a value as to the compound $ASnO_{3-\delta}$ and is measured by the following method. With reference to an electron photomicrographic image of the compound $ASnO_{3-\delta}$, the arithmetic mean of lengths of major axes of crystals and the lengths of minor axes thereof is calculated as a crystallite size. The average of this size for crystal particles is taken as the mean crystallite size.

TABLE 3

Effect of growth of crystals

| No. | Semiconductor and baking temp. (°C.) | Mean crystallite size (μ) | Oxygen gradient*2 700° C. | 800° C. |
|---|---|---|---|---|
| 1 | $BaSnO_{3-\delta}$ 1000° C. | 0.02μ | 0.08 |  |
| 2 | $BaSnO_{3-\delta}$ 1100° C. | 0.08μ | 0.09 |  |
| 3 | $BaSnO_{3-\delta}$ 1200° C. | 0.15μ | 0.17 |  |
| 4 | $BaSnO_{3-\delta}$ 1270° C. | 0.3μ | 0.20 |  |
| 5 | $BaSnO_{3-\delta}$ 1400° C. | 0.6μ | 0.220 | 0.218 |
| 6 | $BaSnO_{3-\delta}$ 1500° C. | 1.5μ | 0.221 |  |
| 7 | $BaSnO_{3-\delta}$ 1650° C. | 6μ | 0.22 |  |
| 8 | $RaSnO_{3-\delta}$ 1400° C. | 1μ | 0.22 | 0.22 |
| 9 | $SrSnO_{3-\delta}$ 1100° C. | 0.1μ |  | −0.02 |
| 10 | $SrSnO_{3-\delta}$ 1200° C. | 0.2μ |  | −0.15 |
| 11 | $SrSnO_{3-\delta}$ 1400° C. | 0.4μ | −0.17 | −0.17 |
| 12 | $CaSnO_{3-\delta}$ 1000° C. | 0.12μ |  | −0.06 |
| 13 | $CaSnO_{3-\delta}$ 1100° C. | 0.3μ |  | −0.15 |
| 14 | $CaSnO_{3-\delta}$ 1400° C. | 2μ | −0.18 | −0.18 |

*1 5 mol % of $SiO_2$ is added to the semiconductor but no noble metal is added.
*2 The value of m as determined from $Rs = K.PO_2^m$ when $O_2$ concentration is changed from 1% to 10%.

Effect of Addition of Noble Metal

As shown in FIG. 1 and Table 2, the addition of noble metal produces little or no influence on the oxygen gradient. Noble metal has an effect to inhibit the sensitivity to combustible gases and hold this sensitivity in balance with the oxygen sensitivity when added to the compound $ASnO_{3-\delta}$ in a small amount of about 30 μg to about 100 μg, calculated as metal, per gram of the compound. However, addition of a large amount, e.g., 10 mg per gram of the compound, impairs the responsiveness to changes of atmosphere.

Figure 2:
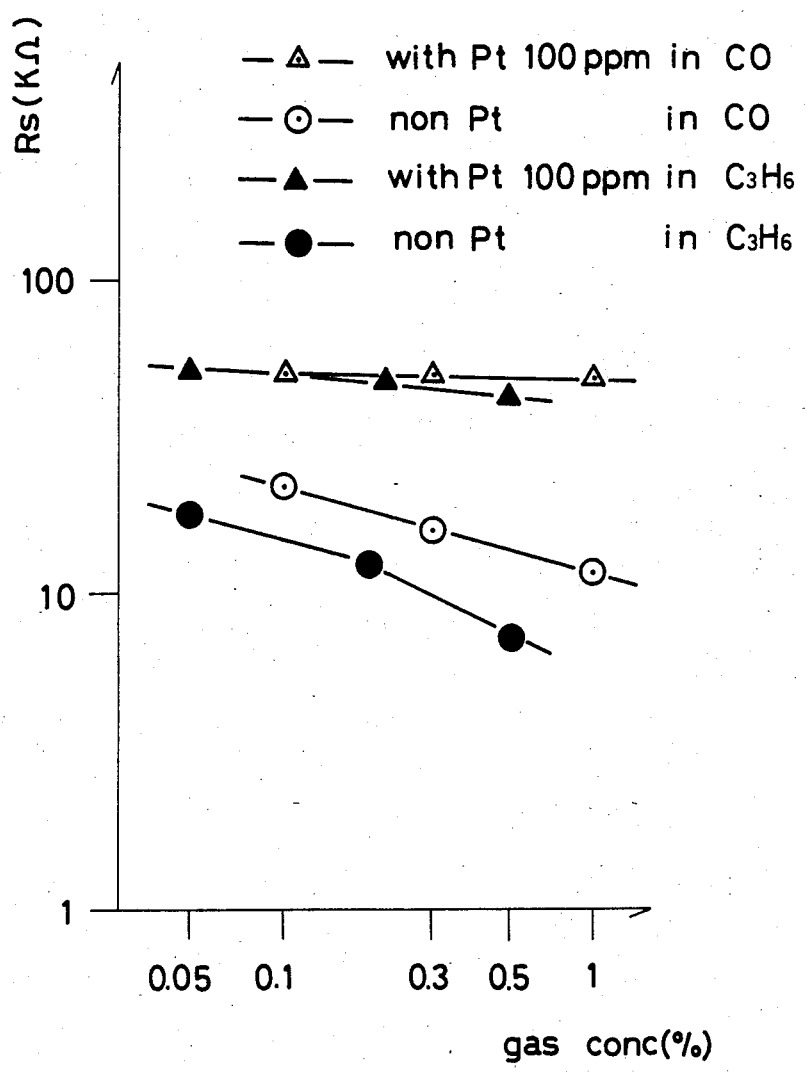
FIG. 2 is a characteristics diagram showing the influence of combustible gas on the resistance value of $BaSnO_{3-\delta}$ having 5 mol % of $SiO_2$ added thereto, as determined in an atmosphere containing 4.6% of $O_2$ at 700° C.

FIG. 2 shows the sensitivity to a combustible gas of $BaSnO_{3-\delta}$ having 5 mol % of $SiO_2$ added thereto and baked at 1400° C. Addition of 100 ppm of Pt inhibits the sensitivity to CO or $C_3H_6$ to hold this sensitivity in balance with the sensitivity to $O_2$. The experimental results shown in the diagram are obtained using an atmosphere containing 4.6% of $O_2$ in balance with $N_2$ and having a temperature of 700° C. at varying CO or $C_3H_6$ concentrations.

Figure 3:
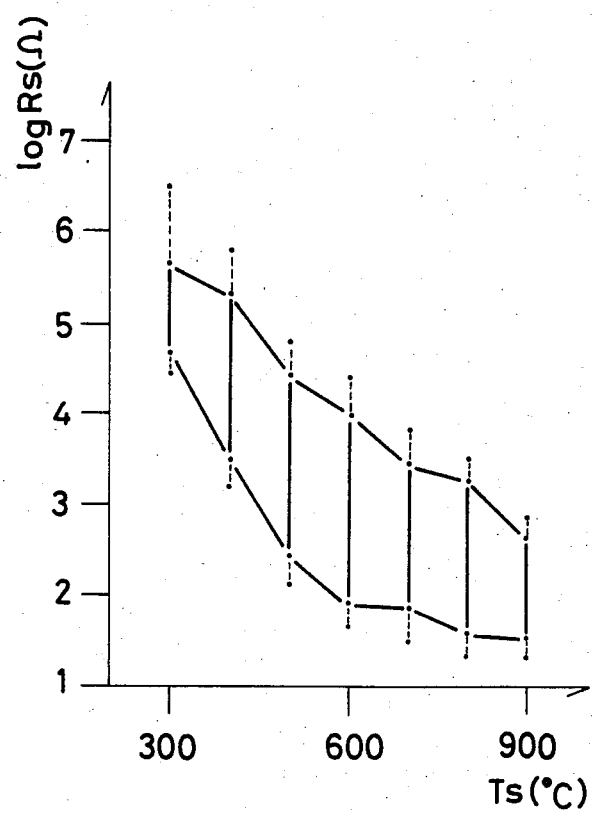
FIG. 3 is a characteristics diagram showing the response of $BaSnO_{3-\delta}$ having 5 mol % of $SiO_2$ and 100 ppm of Pt added thereto, to changes of atmosphere.
Figure 4:
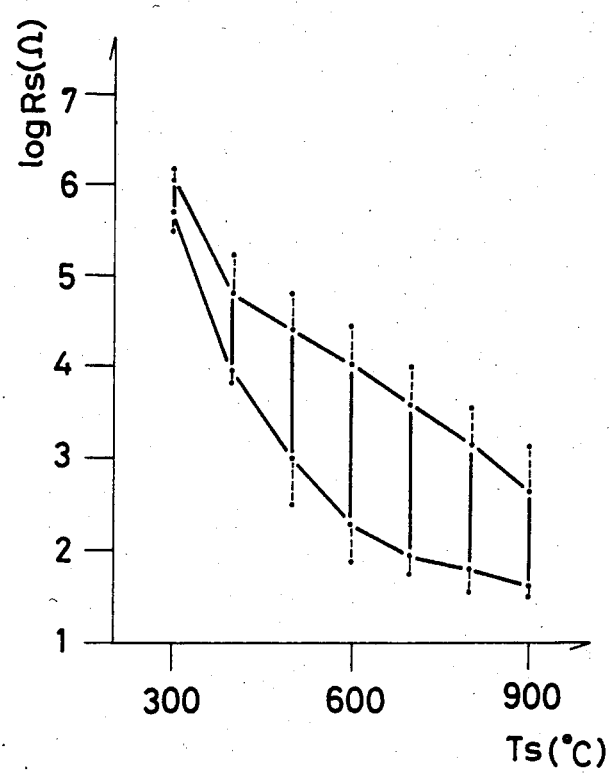
FIG. 4 is a characteristics diagram showing the response of $BaSnO_{3-\delta}$ having 5 mol % of $SiO_2$ and 1000 ppm of Pt added thereto, to changes of atmosphere.
Figure 5:
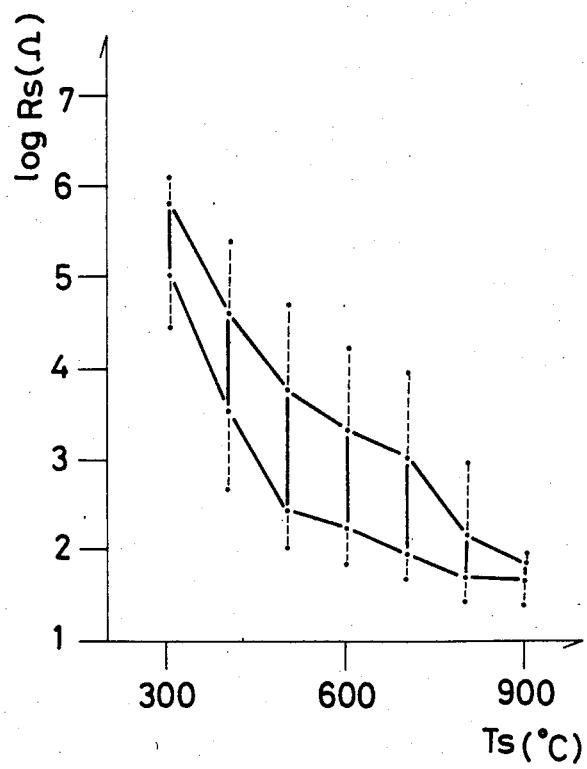
FIG. 5 is a characteristics diagram showing the response of $BaSnO_{3-\delta}$ having 5 mol % of $SiO_2$ and 10,000 ppm of Pt added thereto, to changes of atmosphere.

FIGS. 3, 4 and 5 show the response characteristics to changes of atmosphere as determined using specimens containing 100 ppm, 1000 ppm and 10,000 ppm of Pt, respectively. The specimens are $BaSnO_{3-\delta}$ containing 5 mol of $SiO_2$ and baked at 1400° C.

The flex lines in each diagram represent the variations in the resistance value when the specimen was subjected to repeated cycles of 2-second period including 1 second in an atmosphre of λ=0.99 and 1 second in an atmosphere of λ=1.01. The top points of the broken lines shown represent the variations in the resistance value that occurred when the atmosphere was changed every 3 seconds with a 6-second period. The higher resistance value corresponds to λ=1.01, and the lower value to λ=0.99. Since the presence of a large amount of Pt impairs the responsiveness to changes of atmosphere, it is desirable to use up to 3 mg of Pt per gram of the present compound.

Table 4 shows the effect of addition of noble metal. The table indicates that the combustion gas sensitivity can be inhibited most effectively by Pt, effectively by Rh and moderately by Pd. Other noble metals such as Ru, Ir and Os, a mixture of Pt and Rh, etc. are of course usable. The addition of noble metal is also effective for $RaSnO_{3-\delta}$ containing $SiO_2$, $BaSnO_{3-\delta}$ containing $GeO_2$, and the like.

TABLE 4

Effect of addition of noble metal

| No. | Semiconductor*[1] and amount of $SiO_2$ added | Amount of noble metal added (ppm) | CO sensitivity*[2] and $C_3H_6$ sensitivity (lower value)*[3] | Responsiveness at 900° C. 2-second period*[4] | 6-second period*[5] |
|---|---|---|---|---|---|
| 1 | $BaSnO_{3-\delta}$ 5 mol % |  | 0 | 1.9 | 9 | 30 |
|   |   |   | 2.4 |   |   |
| 2 | $BaSnO_{3-\delta}$ 5 mol % | Pt | 30 | 1.04 | 9 | 30 |
|   |   |   | 1.3 |   |   |
| 3 | $BaSnO_{3-\delta}$ 5 mol % | Pt | 100 | 1.02 | 12 | 32 |
|   |   |   | 1.17 |   |   |
| 4 | $BaSnO_{3-\delta}$ 5 mol % | Pt | 1,000 | 1.02 | 10 | 36 |
|   |   |   | 1.17 |   |   |
| 5 | $BaSnO_{3-\delta}$ 5 mol % | Pt | 10,000 | 1.02 | 1.6 | 4 |
|   |   |   | 1.17 |   |   |
| 6 | $RaSnO_{3-\delta}$ 5 mol % | Pt | 1,000 | 1.02 | 7 | 30 |
|   |   |   | 1.18 |   |   |
| 7 | $SrSnO_{3-\delta}$ 5 mol % | Pt | 1,000 | 0.99 | 6 | 25 |
|   |   |   | 0.92 |   |   |
| 8 | $CaSnO_{3-\delta}$ 5 mol % | Pt | 1,000 | 0.98 | 6 | 23 |
|   |   |   | 0.87 |   |   |
| 9 | $BaSnO_{3-\delta}$ 5 mol % | Pd | 1,000 | 1.03 | 8 | 30 |
|   |   |   | 1.25 |   |   |
| 10 | $BaSnO_{3-\delta}$ 5 mol % | Rh | 1,000 | 1.02 | 9 | 28 |
|   |   |   | 1.18 |   |   |
| 11 | $BaSnO_{3-\delta}$ $GeO_2$ 5 mol % | Pt | 1,000 | 1.03 | 8 | 27 |
|   |   |   | 1.17 |   |   |

*[1] Baked at 1400° C.
*[2] The ratio of the resistance value at 1,000 ppm of CO to that at 10,000 ppm of CO, as determined at 700° C. in a system containing 4.6% of oxygen and $N_2$ in balance.
*[3] The ratio of the resistance value at 500 ppm of $C_3H_6$ to that at 5,000 ppm of $C_3H_6$, as determined in a similar system. When 5,000 ppm of $C_3H_6$ is completely oxidized, the $O_2$ concentration decreases to 23,500 ppm. Ideally, the ratio should be 1.16 for the $BaSnO_3$ system.
*[4] The ratio of the resistance value at λ = 1.01 to that at λ = 0.99 when the specimen is exposed to atmospheres of λ = 0.99 and of λ = 1.01 alternately for 1 second each with a 2-second period.
*[5] The same as above except that the atmosphere is changed every 3 seconds alternately, with a 6-second period.

Figure 6:
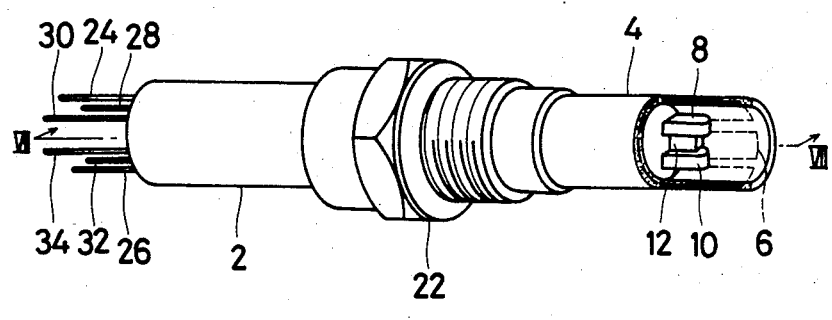
FIG. 6 is a perspective view partly broken away and showing the construction of a λ sensor.
Figure 7:
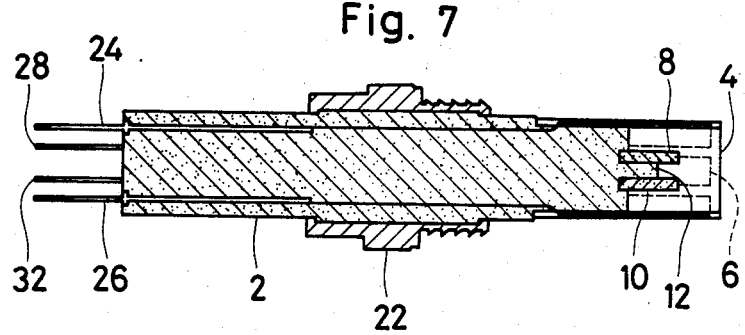
FIG. 7 is a view in section taken along the line VII—VII in FIG. 6.

With reference to FIGS. 6 and 7, the construction of the present λ sensor will be described. Sensors of various constructions are known (as disclosed, for example, in U.S. Pat. Nos. 4,206,647, 4,208,786 and 3,936,794). Thus various constructions other than the illustrated one are usable.

Referring to FIG. 6, a six-hole tubular substrate 2* made of alumina has attached to its forward end a ceramicas tube 4* incorporating a film heater 6* of tungsten, Platinum or the like. The heater 6* serves to heat a gas sensor piece 8* and a temperature sensor piece 10* at a specified temperature. Various heaters other than the illustrated film heater 6 are usable.

In a recessed portion between the substrate *2 and the ceramics tube *4, the gas sensor piece *8 and the temperature sensor piece *10 are provided, with a threshold disposed therebetween. The gas sensor piece *8 is used for the contemplated measuring purpose. The temperature sensor piece is in the form of a thermistor prepared from a catalyst-free semiconductor of the same kind as the gas sensor piece by sintering the material into a compacted piece.

The structure of the gas sensor piece *8 will be described in greater detail with reference to FIG. 8. A porous ceramics block *14 of a compound $ASnO_{3-\delta}$ has embedded therein a pair of noble metal electrodes *16 and *18 and is covered in its entirety with a mullite ($Al_6SiO_2O_{13}$) film *20 about 100 μ in thickness. The mullite film *20 prevents the compound $ASnO_{3-\delta}$ from reacting with the alumina of the substrate *2 to decompose into $AAl_2O_4$ and $SnO_2$. The mullite may be replaced by spinel ($MgAl_2O_4$), cordierite ($Mg_2Al_4Si_5O_{18}$) or the like which will not react with the compound $ASnO_{3-\delta}$. The mullite film 20* is formed preferably by usual coating, spray coating or like method after the addition of silica, noble metal or the like.

The temperature sensor piece *10 may have the same construction as the gas sensor piece *8 except that it is prepared by sintering as a compact structure so as to be held out of contact with gases.

For the gas sensor piece *8 and the temperature sensor piece *10, the same compound $ASnO_{3-\delta}$ may be used, or a combination of different compounds, such as $BaSnO_{3-\delta}$ and $CaSnO_{3-\delta}$, may be used.

Referring to FIGS. 6 and 7 again, indicated at 22 is a metal member for attaching the $\mu$ sensor to the exhaust tube of a motor vehicle engine or to the combustion chamber of an air heater, boiler or the like. Indicated at *4, *26 are lead pins connected to the film heater *6, at *28, *30, lead pins connected to the gas sensor piece 8, and at 32, *34 lead pins connected to the temperature sensor piece 10.

The present invention is not limited to the embodiment described above. For example, $Ba_{0.5}Ra_{0.5}SnO_{3-\delta}$ or like compound is usable. Since the compound $ASnO_{3-\delta}$ is not sensitive to the replacement of the element A or Sn by other elements, such an element may be replaced, for example, by about 10 mol % of some other element. Further the compound $ASnO_{3-\delta}$ may contain other compounds added thereto insofar as the resistance of the present compound predominates the mixture.

What is claimed is:

1. A $\lambda$ sensor comprising a metallic oxide semiconductor whose resistance value is varied by a gas, characterized in that the metallic oxide semiconductor is a compound $ASnO_{3-\delta}$ wherein A is at least one member selected from the group consisting of Ra, Ba, Sr and Ca, and $\delta$ is a non-stoichiometric parameter, the compound $ASnO_{3-\delta}$ having added thereto the dioxide of at least one element selected from the group consisting of silicon, germanium, zirconium and hafnium in an amount of 5 to 300 mmols per mol of the compound $ASnO_{3-\delta}$.

2. A $\lambda$ sensor as defined in claim 1 wherein the additive is silica and is used in an amount of 20 to 300 mmols per mol of the compound $ASnO_{3-\delta}$.

3. A $\lambda$ sensor as defined in claim 2 wherein the amount of the additive is 20 to 200 mmols per mol of the compound $ASnO_{3-\delta}$.

4. A $\lambda$ sensor as defined in any one of claims 1 to 3 wherein the compound $ASnO_{3-\delta}$ is 0.02 to 25 $\mu$ in mean crystallite size.

5. A $\lambda$ sensor as defined in claim 4 wherein the compound $ASnO_{3-\delta}$ is 0.15 to 8 $\mu$ in mean crystallite size.

6. A $\lambda$ sensor as defined in claim 5 wherein the element A of the compound $ASnO_{3-\delta}$ is at least one member selected from the group consisting of element Ba and element Ra.

7. A $\lambda$ sensor as defined in claim 1 or 2 wherein the compound $ASnO_{3-\delta}$ has added thereto 20 $\mu$g to 3 mg of a noble metal per gram of the compound.

8. A $\lambda$ sensor as defined in claim 7 wherein the noble metal is at least one member selected from the group consisting of Pt, Rh, Ir, Os, Ru and Pd.

* * * * *